United States Patent [19]

Syvret

[11] Patent Number: 5,367,071

[45] Date of Patent: Nov. 22, 1994

[54] PROCESS FOR PREPARING DIFLUORINATED DIAZONIABICYCLOALKANE DERIVATIVES

[75] Inventor: Robert G. Syvret, Allentown, Pa.

[73] Assignee: Air Products and Chemicals, Inc., Allentown, Pa.

[21] Appl. No.: 163,254

[22] Filed: Dec. 7, 1993

[51] Int. Cl.$^5$ .................... C07D 487/08; C07B 39/00
[52] U.S. Cl. ................................ 540/472; 540/556; 544/351
[58] Field of Search .................. 344/351; 540/472, 556

[56] References Cited

U.S. PATENT DOCUMENTS

| | | | |
|---|---|---|---|
| 2,964,526 | 12/1960 | Herride | 260/268 |
| 4,935,519 | 6/1990 | Van Der Puy | 547/13 |
| 5,086,178 | 2/1992 | Banks | 544/351 |

FOREIGN PATENT DOCUMENTS 204535  12/1986  European Pat. Off. .

OTHER PUBLICATIONS

Umemoto, Bull Chem Soc. Japan 64, 1081(1991).
Banks, J. Flourine Chem 55, 207(1991).
Specification of 08/163257 (1993).
Bank, J Chem Soc 1992, p. 595.

*Primary Examiner*—Mark L. Berch
*Attorney, Agent, or Firm*—Keith D. Gourley; James C. Simmons; William F. Marsh

[57] ABSTRACT

The invention is a process for preparing 1,4-diazoniabicycloalkanes of Formula I wherein the corresponding 1-hydro-4-aza-1-azoniabi-cycloalkane salt of the 1,4-diazabicycloalkane is fluorinated in the presence of an alkali metal salt under reaction conditions sufficient to form the desired 1,4-diazoniabicycloalkane.

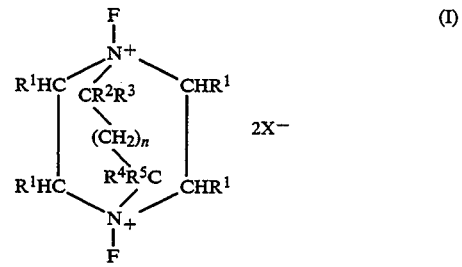

wherein
n represents 0, 1 or 2;
each $R^1$, $R^2$, $R^3$, $R^4$ and $R^5$ independently represents hydrogen, $C_1$–$C_6$ alkyl, aryl, $C_1$–$C_6$ alkyl-substituted aryl or aryl-substituted $C_1$–$C_6$ alkyl; and
each $X^-$ represents a counterion or $2X^-$ represents a single divalent counterion.

7 Claims, No Drawings

PROCESS FOR PREPARING DIFLUORINATED DIAZONIABICYCLOALKANE DERIVATIVES

TECHNICAL FIELD OF THE INVENTION

The present invention relates to a process for preparing novel N,N'-difluorinated diazoniabicycloalkane derivatives which are useful as electrophilic fluorinating agents.

BACKGROUND OF THE INVENTION

A demand exists for fluorinating agents which are site-selective towards organic, especially carbanionic, substrates, especially for use in the preparation of pharmacologically active compounds. A number of such electrophilic fluorinating agents are known but, until recently had limited commercial utility because such agents were expensive, hazardous, inconvenient to handle, unstable and/or insufficiently selective for general use.

Ronald Eric Banks has disclosed in copending U.S. patent application Ser. No. 08/163,257, filed on Dec. 7, 1993 that N,N'-difluorinated diazoniabicycloalkane derivatives of the following Formula I are effective electrophilic fluorinating agents:

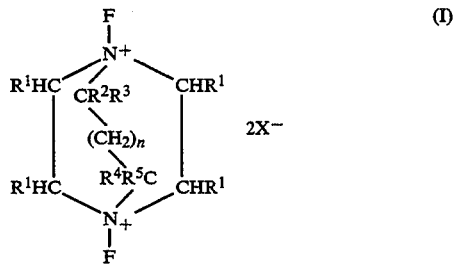

wherein
n represents 0, 1 or 2;
each $R^1$, $R^2$, $R^3$, $R^4$ and $R^5$ independently represents hydrogen, $C_1-C_6$ alkyl, aryl, $C_1-C_6$ alkyl-substituted aryl or aryl-substituted $C_1-C_6$ alkyl; and
each $X^-$ represents a counterion or $2X^-$ represents a single divalent counterion.

Various methods of preparing these compounds are described in the above-mentioned copending patent application. In terms of the 1,4-diazoniabicyclo[2.2.2]octane derivatives (n is 0, and each $R_1$ is hydrogen), the relevant reaction sequences are represented as follows:

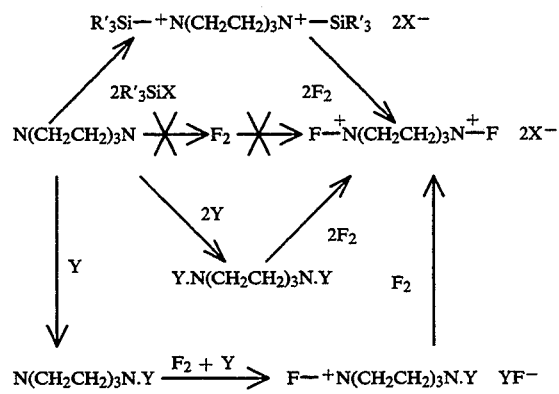

wherein
$R'$ is a $C_1-C_6$ alkyl group,
Y represents a readily fluorinatable Lewis acid,
and X corresponds to the counterion $X^-$ and,
when the relevant compound is formed by fluorination of a Lewis acid adduct, $X^-$ is $YF^-$.
The remaining compounds of Formula I are prepared from analogous reactants.

1,4-Diazabicyclo[2.2.2]octane (otherwise tetraethylenediamine, TEDA) is commercially available under, for example, the Trade Mark DABCO (Air Products and Chemicals Inc.) for use in the manufacture of urethane foams, elastomers and coatings, epoxy resins, and the like articles. N,N-Tetrahalo-1,4-diazoniabicyclo[2.2.2]-octanes in which the halogen is chlorine, bromine or iodine are known and can readily be prepared from 1,4-diazabicyclo[2.2.2]octane by, for example, treatment with the halogen in carbon tetrachloride (see U.S. Pat. No. 2,964,526).

However, the corresponding tetrafluoro compound is unknown and cannot be prepared in an analogous manner. Attempts to fluorinate 1,4-diazabicyclo[2.2.2]octane with fluorine to produce 1,4-difluoro-1,4-diazoniabicyclo[2.2.2]octane difluoride gave an unidentified white solid which showed some fluorinating capacity but readily decomposed at ambient temperature into a coloured material having no electrophilic fluorinating power.

SUMMARY OF THE INVENTION

Applicant has unexpectedly discovered that the 1,4-difluoro-1,4-diazoniabicycloalkanes of Formula I can be prepared by fluorinating the corresponding 1-hydro-4-aza-1-azoniabicycloalkane salts in the presence of an alkali metal salt under enumerated reaction conditions. Specifically, the process comprises contacting such corresponding 1-hydro-4-aza-1-azoniabicycloalkane salts with fluorine in the presence of an alkali metal salt under reaction conditions sufficient to form the 1,4-difluoro-1,4-diazoniabicycloalkanes of Formula I and recovering the same from the resulting reaction mixture.

The fluorinations can be carried out using a stirred-tank batch reactor into which the fluorine is admitted either as a single charge of the gas at sub-atmospheric pressure or as a continuous flow of fluorine blended with nitrogen or other inert diluent at about atmospheric pressure.

DETAILED DESCRIPTION OF THE INVENTION

According to the present invention, Applicant presents a process for preparing N,N'-difluorinated diazoniabicyclo-alkane derivatives of the following Formula I:

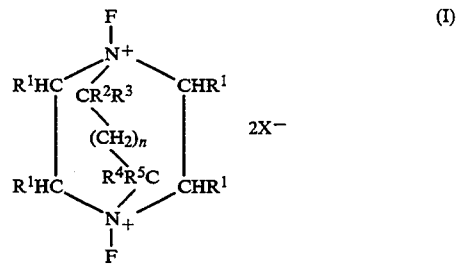

wherein
n represents 0, 1 or 2;
each $R^1$, $R^2$, $R^3$, $R^4$ and $R^5$ independently represents hydrogen, $C_1-C_6$ alkyl, aryl, $C_1-C_6$ alkyl-substituted aryl or aryl-substituted $C_1-C_6$ alkyl; and
each $X^-$ represents a counterion or $2X^-$ represents a single divalent counterion.

The process for preparing the derivatives according to Formula I comprises fluorinating the corresponding 1-hydro-4-aza-1-azoniabicycloalkane salts of the following Formula II:

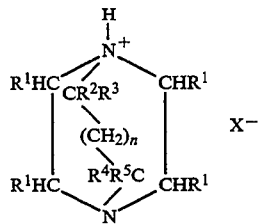
(II)

wherein n, $R^1$, $R^2$, $R^3$, $R^4$, $R^5$, and $X^-$ are as defined above, in the presence of an alkali metal salt $M^+X^-$, wherein $X^-$ is as defined above and $M^+$ is an alkali metal cation.

When any of $R^1$ to $R^5$ is other than hydrogen, it is preferably benzyl, phenyl or, especially, $C_1-C_4$ alkyl, particularly methyl. However, due to steric considerations it may not be possible to obtain compounds with all possible combinations of $R^1$ to $R^5$ values.

Usually no more than one $R^1$ at the 2 and 3 ring positions and no more than one $R^1$ at the 5 and 6 ring positions will be other than hydrogen. It is preferred that all $R^1$ are hydrogen.

Usually no more than one of $R^2$, $R^3$, $R^4$ and $R^5$ is other than hydrogen. It is preferred that all of $R^2$ to $R^5$ are hydrogen.

It is especially preferred that n is 0, and each $R_1$ is hydrogen (i.e. that the compounds of Formula II are derivatives of 1,4-diazabicyclo[2.2.2]octane. Thus, according to a preferred embodiment, the 1-hydro-4-aza-1-azoniabicycloalkane salts of Formula II are of the following Formula III $$H-{}^+N(CH_2CH_2)_3N\ X^-$$ (III)

wherein $X^-$ is as defined above.

The counterion represented by $X^-$ in Formulae I to III can be any anion which can be a counterion to the quaternizing fluorine. Usually, but not necessarily, the counterion will be weakly nucleophilic.

Suitable anions include halides, especially fluoride ($F^-$); fluorosulfate ($SO_3F^-$); alkanesulfonates, especially methanesulfonate ($CH_3SO_3^-$); alkyl sulfates, especially methyl sulphate ($CH_3SO_4^-$); perfluoroalkane-sulfonates, preferably triflate ($CF_3SO_3^-$) and nonaflate ($C_4F_9SO_3^-$); arenesulfonates, especially tosylate (i.e. p-toluene-sulfonate; $CH_3C_6H_4SO_3^-$); alkanecarboxylates; perfluoroalkanecarboxylates; tetrafluoroborate ($BF_4^-$); tetraphenylborate ($Ph_4B^-$); hexafluorophosphate ($PF_6^-$); hexafluoroantimonate ($SbF_6^-$); chlorate ($ClO_3^-$); and sulfate ($SO_4^-=2X^-$). The preferred anions are fluoride, triflate, tosylate and, especially, tetrafluoroborate.

The fluorinations usually are carried out using a stirred-tank batch reactor into which the fluorine is admitted either as a single charge of the gas at sub-atmospheric pressure or as a continuous flow of fluorine blended with nitrogen or other inert diluent at about atmospheric pressure.

In the first of said fluorination methods, fluorine, usually diluted with nitrogen, is passed into a stirred low temperature solution or suspension of the 1-hydro-4-aza-1-azoniabicycloalkane salts of Formula II in a suitable organic solvent, for example trichlorofluoromethane or especially acetonitrile. Usually, the temperature is in the range −35° C. to −78° C. and the fluorine pressure is below 20 mmHg (2.7 kPa).

In the second fluorination method, fluorine heavily diluted with an inert gas, usually nitrogen, is passed through said solution at about ambient pressure (see U.S. Pat. Nos. 4,479,901 and 5,086,178).

The fluorination is conducted in the presence of an alkali metal salt $M^+X^-$, wherein $X^-$ is as defined above and $M^+$ is an alkali metal cation, usually lithium.

Preferably, both the heterocyclic and alkali metal salts are triflates (i.e. trifluoromethane-sulfonates) and the reaction is conducted in acetonitrile under nitrogen.

The 1-hydro-4-aza-1-azoniabicycloalkane salts of Formula II can readily be prepared by treating in a suitable organic solvent the corresponding 1,4-diazabicyclo[2.2.2]alkane of the following Formula IV

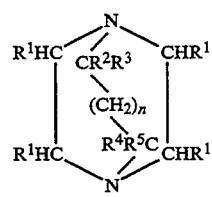
(IV)

wherein n, $R^1$, $R^2$, $R^3$, $R^4$, $R^5$, and $X^-$ are as defined above, with the corresponding acid $H^+X^-$, wherein X is as defined above. Usually, the 1,4-diazabicyclo[2.2.2-]alkane is stoichiometrically titrated with acid in the solvent to be used for the subsequent fluorination and the 1-hydro-4-aza-1-azoniabicycloalkane salts fluorinated in situ.

The 1,4-diazabicyclo[2.2.2]alkanes of Formula IV are known per se or can be prepared by analogous methods to those known per se. In particular, those compounds of Formula IV in which n is 0 can be obtained by acid-catalyzed ring closure of the corresponding N-(hydroxyethyl) piperazine. The N-(hydroxyethyl) piperazines can be obtained by reaction of the corresponding piperazine with ethylene oxide or an appropriately substituted ethylene oxide. Substituted piperazine reactants can be obtained by reaction of an ethanolamine, an ethylene oxide and ammonia with the ethanolamine and/or ethylene oxide being appropriately substituted. The diazabicyclononane derivatives in which n is 1 or 2 can be obtained by treatment of the corresponding piperazine or homopiperazine with an appropriate alkyldihalide.

The fluorinating agents of Formula I are used in manner know per se as electrophilic fluorinating agents (see, for example, R. E. Banks et al J. Chem. Soc. Perkin Trans. I, 1988, 2805). They appear to be unstable in the presence of moisture and hence should be protected from atmospheric moisture by, for example, storage under dry nitrogen in polyalkene or similar containers resistant to hydrogen fluoride.

The invention is illustrated by the following non-limiting Example.

EXAMPLE 1

1,4-Difluoro-1,4-diazoniabicyclo[2.2.2]octane bistriflate

Step A 1-hydro-4-aza-1-azoniabicyclo[2.2.2]octane triflate

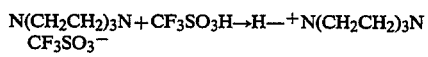

1,4-Diazabicyclo[2.2.2]octane was stoichiometrically titrated in acetonitrile solution with neat trifluoromethanesulfonic acid. The stoichiometric endpoint (at pH=5.851) was monitored by potentiometric methods. Analysis of the resulting acetonitrile solution by $^1$H and $^{19}$F NMR spectroscopy was consistent with 1-hydro-4-aza-1-azonia-bicycloalkane[2.2.2]octane triflate (concentration 0.505 mmol cm$^{-3}$).

Step B 1,4-Difluoro-1,4-diazoniabicyclo[2.2.2]octane bistriflate $$H-{}^+N(CH_2CH_2)_3NCF_3SO_3^- \xrightarrow[CF_3SO_3Li]{F_2}$$

$$F-{}^+N(CH_2CH_2)_3N^+-F(CF_3SO_3^-)_2$$

All operations were performed under an atmosphere of dry nitrogen. An aliquot (50 cm$^3$) of the solution prepared in Step A (containing 25.25 mmol of 1-hydro-4-aza-1-azonia-bicycloalkane[2.2.2]octane triflate) was diluted to 550 cm$^3$ with anhydrous acetonitrile (final concentration 0.046M) in a jacketed glass reactor. To this solution was added 8.51 g (54.6 mmol) of lithium triflate and the mixture was cooled to $-45°$ C. while being stirred. Fluorine diluted with nitrogen (ca. 6% by volume of $F_2$ in $N_2$) was then introduced through a sparging dip-tube at the rate of 200 cm$^3$ per minute until a total of 70.4 mmol of $F_2$ had passed into the mixture (ca. 2.5 hours). The reactor was then purged with nitrogen for a period of 10 minutes, and the reaction solution allowed to stand to allow solid matter to settle. The clear supernatant liquid was then decanted into a polyethylene container, which was subsequently tightly sealed and cooled to $-78°$ C. The mixture was kept at this temperature for the duration of analysis and evaluation.

The product in solution was characterized by iodometric analysis and low-temperature multinuclear magnetic resonance ($^1$H, $^{13}$C, $^{19}$F) spectroscopy. The $^1$H, $^{19}$F and $^{13}$C NMR spectra were recorded at $-42°$ C. and were fully consistent with 1,4-difluoro-1,4-diazoniabicyclo[2.2.2]octane bistriflate. Thus the $^1$H spectrum comprised a broadened 12H multiplet at 4.93 p.p.m. [six equivalent CH$_2$ groups, each magnetically coupled (partially resolved) to two equivalent N$^+$—F groups], and a singlet at 3.52 p.p.m. due to unreacted starting material. With CFCl$_3$ as reference, the $^{19}$F spectrum showed two singlets of relative intensities 2:3 at 36.62 p.p.m. (two equivalent N$^+$—F groups) and $-79.12$ p.p.m. (CF$_3$SO$_3^-$). The $^{13}$C spectrum comprised a doublet-of-doublets, at 60.52 p.p.m. corresponding to the six CH$_2$ groups of the difluoro compound, a triflate quartet at 121.21 p.p.m., and a singlet at 44.20 p.p.m. caused by the presence of some unreacted starting material.

I claim:

1. A process for preparing N,N'-difluorinated diazoniabicyclo-alkane derivatives represented by the Formula (I)

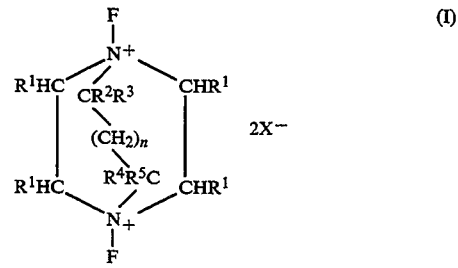

wherein
n represents 0, 1 or 2;
each $R^1$, $R^2$, $R^3$, $R^4$ and $R^5$ independently represents hydrogen, $C_1$–$C_6$ alkyl, aryl, $C_1$–$C_6$ alkyl-substituted aryl or aryl-substituted $C_1$–$C_6$ alkyl; and
each $X^-$ represents a counterion or $2X^-$ represents a single divalent counterion,
which process comprises fluorinating the corresponding 1-hydro-4-aza-1-azoniabicycloalkane salts of the following Formula (II)

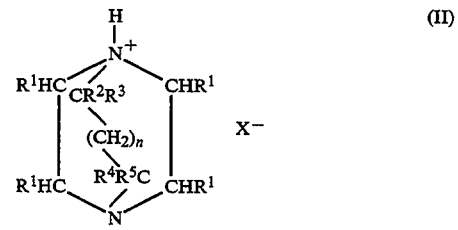

wherein n, $R^1$, $R^2$, $R^3$, $R^4$, $R^5$, and $X^-$ are as defined above, in the presence of an alkali metal salt $M^+X^-$, wherein $X^-$ is as defined above and $M^+$ is an alkali metal cation.

2. The process according to claim 1, wherein n is 0 and each $R^1$ to $R^5$ is hydrogen.

3. The process according to claim 1, wherein $X^-$ is selected from the group consisting of fluoride; fluorosulfate; methanesulfonate; methyl sulfate; triflate; nonaflate; tosylate; tetrafluoroborate; tetraphenylborate; hexafluorophosphate; chlorate, and hexafluoroantimonate.

4. The process according to claim 3, wherein $X^-$ is selected from the group consisting of tetrafluoroborate, tosylate and triflate.

5. The process according to claim 4, wherein both $X^-$ are triflates.

6. The process according to claim 1, wherein fluorine diluted with nitrogen is passed into a stirred low temperature solution or suspension of the 1-hydro-4-aza-1-azoniabicycloalkane salt of Formula II in a suitable organic solvent.

7. The process according to claim 6, wherein the solvent is trichlorofluoromethane or acetonitrile.

* * * * *